United States Patent
Rao et al.

(10) Patent No.: US 6,537,593 B2
(45) Date of Patent: Mar. 25, 2003

(54) PLANT PHENOL AS NEW HEPATOPROTECTIVE AGENTS

(75) Inventors: Janaswamy Madhusudana Rao, Andhra Pradesh (IN); Ashok Kumar Tiwari, Andhra Pradesh (IN); Pullela Venkata Srinivas, Andhra Pradesh (IN); Jhillu Singh Yadav, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/058,088

(22) Filed: Jan. 29, 2002

(65) Prior Publication Data

US 2002/0094351 A1 Jul. 18, 2002

Related U.S. Application Data

(62) Division of application No. 09/698,176, filed on Oct. 30, 2000, now abandoned.

(51) Int. Cl.$^7$ .......................... A61K 35/78; A61K 31/34
(52) U.S. Cl. ........................ 424/769; 424/770; 424/725; 514/461; 514/468
(58) Field of Search ................................. 424/725, 769, 424/770; 514/461, 468

(56) References Cited

PUBLICATIONS

Khamlach et al., Tetrahedron, vol. 48, No. 46, pp. 10115–10126, 1992.
Suga et al., Phytochemistry, vol. 33, No. 6, pp. 1395–1401, 1993.
Kawai et al., Phytochemistry, vol. 51, No. 2, pp. 243–247, May 1999.
Achenbach et al., Phytochemistry, vol. 22, pp. 749–753, 1983.

*Primary Examiner*—Christopher R. Tate
(74) *Attorney, Agent, or Firm*—Birch, Stewart, Kolasch & Birch, LLP

(57) ABSTRACT

This invention relates to the isolation of compound namely (−)-wikstromol and together with or associated with a therapeutically acceptable additive and useful as hepatoprotective agent.

16 Claims, 2 Drawing Sheets

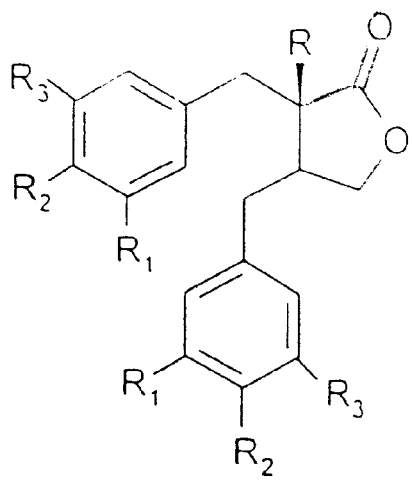
Fig.1(a)
R = R$_1$ = R$_2$ = H or OH, R$_3$ = OMe
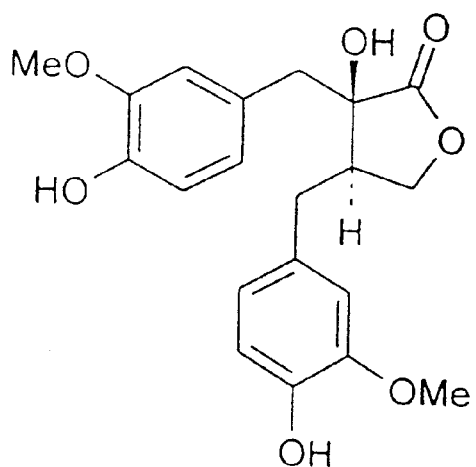
Fig.1(b)
(−)-Wikstromol
FIG.1

PLANT PHENOL AS NEW HEPATOPROTECTIVE AGENTS

This is a Divisional application of Ser. No. 09/698,176, filed Oct. 30, 2000, now abandoned.

FIELD OF THE INVENTION

This invention relates to the isolation of a compound namely (−)-wikstromol (4,4$^1$,8-trihydroxy-3,3$^1$-dimethoxyliganan-9,9$^1$-olide) from a plant source *Cedrus deodara* in significant yields. This invention also identifies the use of the compound as a hepatoprotective agent.

PRIOR ART

The compound (−)-wikstromol as such does not find much commercial value. The structural formula of (−)-wikstromol is shown in FIG. 1. Lignans are widely distributed in angiosperms and gymnosperms. The range of their structures and biological activities is broad. (−)-Wikstromol is found to be active against p-388 lymphocyte leukemia and anti-HIV activity (M. K. Khamlach, R. Dhal and E. Brown). [Premieres syntheses totales du (+)-wikstromol, de la (−)-Trachelogenine, De la (−)-Nortrachelogenine et des lignoides apparentes—Tetrahedran 48, 10115–10126 (1992)].

The wood of *Cedrus deodara* possesses diaphoretic, diuretic and carminative properties, and it is useful in treatment of fevers, piles and pulmonary and urinary disorders. The extract of the bark is astringent and useful for fevers, diarrhea and dysentery. The oleoresin of deodar and the dark-colored oil obtained from the wood are valued for their application for ulcers and skin diseases. [Ref: Wealth of India, Vol. II, P.108–10 (1950) (published by CSIR)].

A close look at literature suggests that the lignan, sec-oisolariciresinalldeglycoside (SDG) which has been reported to possess a multitude of activities is isolated from flaxseed [U.S. Pat. No. 5,846,944].

P. K. Agarwal and R. P. Rastogi (Phytochemistry vol. 21, No. 6, pp. 1459–1461, 1982) reported isolation of two lignans meso-secoisolariciresinol and cedrusinin from *Cedrus deodara*.

The isolation of matariesional in 0.10% yield and (+)-wikstromol in 0.124% yield is reported from *Wikstroemia viridiflora* (Wikstromol, a new lignan from *Wikstroemia viridiflora*—Sheela Tandon and R. P. Rastogi; Phytochemistry 1976, vol. 15, pp. 1789–1791).

The extraction of the lignans and other constituents namely (−)-nortrachelogenin, carinol and carissanol from *Carissa edulis* is reported by Hans Achenbach, Reiner Waibel and Ivan Addae-Mensah, in Phytochemistry, Vol.22, No.3, pp.749–753, 1983.

There is a considerable amount of epidemiological evidence indicating an association between diets rich in fruits and vegetables and a decreased risk of cardiovascular disease and certain forms of cancer. It is generally assumed that the active principles contributing to these protective effects are nothing but antioxidant phytochemicals.

Recent research has been directed to find out the phytochemicals from plant sources and to highlight the role of polyphenolic compounds of plant materials as antioxidants, antimutagenic, anti inflammatory, antiatherosclerotic, antidiabetic, antihepatotoxic and antimicrobial agents. [An overview of flax lignans is given by Neil D. Westcott and Alister D. Muir, Crop Utilization Section, Saskatoon Research Centre, Agriculture and Agri-Food Canada, 107, Science Place, Saskatoon, SK S7N 0X2, Canada in vol. II—January 2000 —inform]. The alcoholic extract of stem *C. deodara* was found to have anti-cancer activity. [See Medicinal Plants of India (ICMR) Vol. I, 1976, pp.214 and 215].

Accordingly, the applicants conducted a detailed study on principles from *Cedrus deodara* and this investigation led to the isolation of active principles, namely, wikstromol. These compounds although hitherto isolated from Wikstromia spp. were in low yields. *Cedrus deodara*, hence, is a new source for the lignans and its presence in this taxon in significantly high yields makes this invention more important.

OBJECTS OF THE INVENTION

The main object of the invention is to provide novel compositions containing (−)-wikstromol which are useful as a hepatoprotective agent.

Yet another object of the invention is to provide methods for the isolation of (−)-wikstromol from *Cedrus deodara*.

SUMMARY OF THE INVENTION

Accordingly, the invention provides novel compositions containing (−)-wikstromol which are useful as hepatoprotective agents. The invention further provides method for the isolation of (−)-wikstromol from *Cedrus deodara*.

DETAILED DESCRIPTION

Accordingly, the invention provides a composition comprising an effective amount of (−)-wikstromol together with or associated with an additive and useful as a hepatoprotective agent.

In an embodiment, the additive is selected in such a manner that it does not affect or interfere with the efficacy of the active principles of the composition. The additives are such that they enhance and do not retard the activity of the active ingredient, i.e. (−)-wikstromol.

In another embodiment, the additive is selected from nutrients such as carbohydrates, sugar, proteins and pharmaceutically acceptable carriers.

In still another embodiment, the ratio of (−)-wikstromol with the additive is in the range between 0.4:10 to 2.0:10.

In yet another embodiment, (−)-wikstromol is present in an amount of 250–300 mg.

Further, the invention provides a process for the isolation of (−)-wikstromol from the *Cedrus deodara*, said process comprising the steps of:

g) extraction of the pulverized plant parts of *Cedrus deodara* with solvents to remove the essential oils;

h) concentrating the extract under vacuum to obtain a residue;

i) adding ethyl acetate to the residue obtained in step (b);

j) separating the solvents by conventional methods;

k) subjecting the residue to a first elution with about 3% methanol in chloroform to obtain (−)-matairesinol; and l) subjecting the residue of step (e) to a second elution with about 5% methanol to obtain (−)-wikstromol.

The solvents used in step (a) are hexane and chloroform.

In another embodiment, the plant parts of *Cedrus deodara* such as bark and leaves are used for extraction.

In yet another embodiment, the wasted plant parts of *Cedrus deodara* are employed for isolation of the said compound. Preferably, the waste left, after extraction of essential oil from the plant parts, is used in the process.

Accordingly, the compositions prepared can be used as hepatoprotective treatment agents, wherein an effective amount of (−)-wikstromol is administered to a subject in need thereof.

(−)-Wikstromol may be administered together with or in combination with therapeutically acceptable additives. The effective amount of (−)-wikstromol that may be administered to a subject can be readily determined by a person skilled in the art. However, it is recommended that the dosage of (−)-wikstromol administered may be in the range of 250 to 300 mg per dose, twice a day. While it is possible to administer the composition in many routes, the oral route achieves the desired, best results.

Compositions employing (−)-wikstromol may be prepared by conventional methods as may be known in the art. The compositions may be in the form of tablets, capsules or syrups, etc. Suitable additives as may be known in the art may be selected for the preparation of these compositions.

In essence, the focus of the invention is to provide methods for using (−)-wikstromol for the preparation of compositions useful as hepatoprotective agents.

The heartwood of *Cedrus deodara* finds extensive use in the essential oil industry. The oil named 'cedar wood' oil finds applications in flavor and fragrances. The heartwood powder, after extraction of the essential oil, is a by-product and waste.

This invention relates to isolation and purification of the compound (−)-wikstromol, which is useful as a hepatoprotective agent.

The present invention relates to the isolation of a compound, namely (−)-wikstromol (4,4$^1$,8-trihydroxy-3,3$^1$-dimethoxyliganan-9,9$^1$-olide) from a new plant, *Cedrus deodara*. This invention also relates to a new use of the compound, i.e., as a hepatoprotective agent.

The present invention embodies the isolation of (−)-wikstromol, an antioxidant principle from an entirely new source and its superior antihepatotoxic property compared with known biologically proved anti hepatotoxic agents.

BRIEF DESCRIPTION OF DRAWINGS

The accompanying diagrams illustrate the invention wherein:

FIG. 1(*a*): represents hydroxyl substituted 3,3$^1$-dimethoxylignan-9,9$^1$-olide.

FIG. 1(*b*): represents (−)-wikstromol (4,4$^1$,8-trihydroxy-3,3$^1$-dimethoxyliganan-9,9$^1$-olide).

Figure 2:
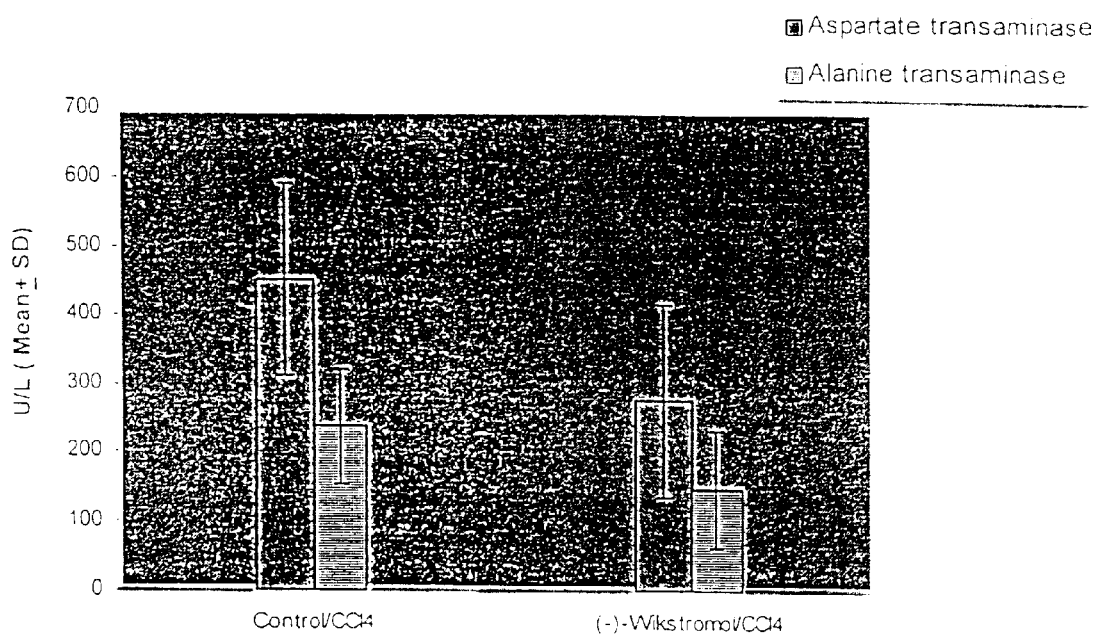
FIG. 2: is the graphical representation of the hepatoprotective activity of (−)-Wikstromol.

Some of the embodiments of the present invention are presented by the following examples, which should not be construed as limitations on the inventive scope of the invention.

EXAMPLE 1

Experimental Protocols: A Process for the Isolation of Wikstromol

The dried wood powder of *Cedrus deodara* was loaded 200 g in a soxhlet apparatus. The powder was first extracted with hexane to remove the essential oil composition. The residue from the extraction of hexane was further extracted with chloroform. The chloroform extract was concentrated under vacuum. The thick syrupy residue was dissolved in ethyl acetate for a total of about 50 g of residue in about 60 ml of ethyl acetate. The isolation of residue in ethyl acetate was added drop wise to hexane 9 around 5Lt. The solid separated (35 g) was filtered off.

The solid was loaded on a silica gel column 60–120 mesh, 3.5 cm in diameter. The column was loaded to a height of 60 cm. Initially, the column was eluted with chloroform followed by 3% methanol in chloroform to get Matairesinol.

Further elution of the column with 5% methanol in chloroform yielded (−)-Wikstromol.

The yield of (−) wikstromol is around 8.0 g.

The compound (−)-wikstromol is obtained in 90% purity.

The spectrochemical and physical properties of (−)-wikstromol are as follows:

(−)-Wikstromol

6. Molecular formula: $C_{20}H_{22}O_7$
7. $^1$H-NMR: δ2.40–2.55(2H, m), 2.65–2.80 (2H, m), 3.10–3.20(1H, d), 3.85(6H, d), 3.95(2H,br d) 5.60(2H, d), 6.50–6.80(6H, m)
8. $^{13}$C-NMR: δ31.50(C-7), 41.90(C-8), 43.74(C-7), 55.94 (2X-OMe), 70.26(O—CH$_2$—O), 76.33(—C—OH) 111.55, 112.81, 114.35, 114.56, 116.82, 121.42, 123.12, 126.20, 130.35, 144.27, 144.95, 146.59(12 X Ar—C)
9. MS: 374 (M$^+$)
10. $[α]_D$: −30.90 (28° C.)

EXAMPLE 2

Carbon tetrachloride is a classical method to induce free radical mediated hepatotoxicity. In order to evaluate the free radical mediated hepatotoxicity and heptoprotective properties in the compound (−)-wikstromol, this method was employed. Male wistar rats were selected for study. The compound was dissolved in a small amount of DMSO and reconstituted in gum acacia/water. The compound was given one hour before CCl$_4$ administration to the over-night fasted rats in a dose of 250 mg/kg-body weight, orally. After one hour, a mixture of CCl$_4$ and liquid paraffin (1:1, v/v) in the dose of 2.5 ml/kg was given orally. Fasting was continued. However, water was provided ad-libitum. After 5 hrs of CCl$_4$ administration, blood was taken out from the retroorbital plexus. Serum aspartase transaminase and serum alanine transaminase was measured as a marker of hepatotoxicity. Table 1 and FIG. 2 show significant protection offered by the compound, (−)-wikstromol. FIG. 2 shows that (−)-wikstromol significantly prevented CCl$_4$ induced toxicity in rats.

TABLE 1

| | AST (U/L) | | ALT (U/L) | |
|---|---|---|---|---|
| | Before | After | Before | After |
| CCl$_4$ control | 233 ± 139 (10) | 686 ± 142 (10) | 37 ± 9 (10) | 273 ± 80 (10) |
| (−) - Wikstromol Treated + CCl$_4$ | 281 ± 91 (5) | 557 ± 126 (5) | 42 ± 7 (5) | 188 ± 66 (5) |

Serum Aspartate transaminase (AST) and Alanine transaminase (ALT) status before oral administration of compound and CCl$_4$ and 5 hours after administration. (values are mean ± SD, no. in parenthesis are no. of animals in each group).

EXAMPLE 3

Carbon tetrachloride induced toxicity was repeated as referred in the example 2 by changing the dosage level to 300 mg/kg-body weight, orally. Fasting was continued. However, water was provided ad-libitum. After 5hrs of CCl$_4$ administration, blood was taken out from the retroorbital plexus. Serum aspartase transaminase and serum alanine transaminase was measured as a marker of hepatotoxicity. The (−)-wikstromol shows significant activity and prevented CCl₄ induced toxicity in rats.

In accordance with the practice of this invention, it has been found that (−)-wikstromol is isolated from a new plant source *Cedrus deodara* in significant yields. Also, it has been found that (−)-wikstromol shows hepatoprotective properties.

ADVANTAGES

The compound (−)-wikstromol is used in pure form.

Hence, the usage is more advantageous than a mixture of compounds having similar properties, which are in current use. It is also important to note that the process of isolation of (−)-wikstromol is highly economical wherein it subsequently can be used as a hepatoprotective agent.

(−)-Wikstromol is used at a high degree of purity of over 90%. It has been found to be highly effective when administered at a dosage of 250 to 300 mg/kg of body weight.

What is claimed is:

1. A method for preventing free radical mediated hepatotoxicity comprising administering to a subject in need thereof an effective amount of a composition comprising (−)-wikstromol.

2. The method of claim 1, wherein the composition further comprises an additive selected from the group consisting of a carbohydrate, a protein and a pharmaceutically acceptable carrier, and mixtures thereof.

3. The method of claim 2, wherein the ratio of (−)-wikstromol to additive is in the range from 0.4:10 to 1:5.

4. The method of claim 1 wherein the amount of (−)-wikstromol that is administered is in the range from 250 to 300 mg per dose.

5. The method of claim 2 wherein the amount of (−)-wikstromol that is administered is in the range from 250 to 300 mg per dose.

6. The method of claim 3 wherein the amount of (−)-wikstromol that is administered is in the range from 250 to 300 mg per dose.

7. The method of claim 1, wherein the composition is administered twice per day.

8. The method of claim 2, wherein the composition is administered twice per day.

9. The method of claim 3, wherein the composition is administered twice per day.

10. The method of claim 4, wherein the composition is administered twice per day.

11. The method of claim 5, wherein the composition is administered twice per day.

12. The method of claim 6, wherein the composition is administered twice per day.

13. The method of claim 1, wherein the composition is administered orally.

14. The method of claim 6, wherein the composition is administered orally.

15. The method of claim 7, wherein the composition is administered orally.

16. The method of claim 12, wherein the composition is administered orally.

* * * * *